(12) United States Patent
Mitschke et al.

(10) Patent No.: US 7,010,080 B2
(45) Date of Patent: Mar. 7, 2006

(54) METHOD FOR MARKER-FREE AUTOMATIC FUSION OF 2-D FLUOROSCOPIC C-ARM IMAGES WITH PREOPERATIVE 3D IMAGES USING AN INTRAOPERATIVELY OBTAINED 3D DATA RECORD

(75) Inventors: Matthias Mitschke, Nünberg (DE); Norbert Rahn, Forchheim (DE); Dieter Ritter, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 70 days.

(21) Appl. No.: 10/850,499

(22) Filed: May 20, 2004

(65) Prior Publication Data

US 2005/0004454 A1    Jan. 6, 2005

(30) Foreign Application Priority Data

May 20, 2003 (DE) ................................ 103 22 738

(51) Int. Cl.
*A61B 6/03* (2006.01)
(52) U.S. Cl. .................. 378/8; 378/8; 378/15; 378/901
(58) Field of Classification Search .................... 378/4, 378/8, 15, 19, 901
See application file for complete search history.

(56) References Cited

U.S. PATENT DOCUMENTS

| 5,852,646 A | 12/1998 | Klotz et al. |
|---|---|---|
| 6,628,977 B1 | 9/2003 | Graumann et al. |
| 6,837,892 B1 * | 1/2005 | Shoham ...................... 606/130 |
| 2003/0181809 A1 | 9/2003 | Hall et al. |
| 2003/0220555 A1 * | 11/2003 | Heigl et al. .................. 600/407 |
| 2005/0004449 A1 * | 1/2005 | Mitschke et al. ........... 600/424 |

* cited by examiner

*Primary Examiner*—David V Bruce
(74) *Attorney, Agent, or Firm*—Schiff Hardin LLP

(57) ABSTRACT

In a method and apparatus for automatic marker-free fusion (matching) of 2D fluoroscopic C-arm images with preoperative 3D images using an intraoperatively acquired 3D data record, an intraoperative 3D image is obtained using a C-arm x-ray system, image-based matching of an existing preoperative 3D image in relation to the intraoperative 3D image is undertaken, which generates a matching matrix of a tool plate attached to the C-arm system is matched in relation to a navigation system, a 2D fluoroscopic image to be matched is obtained, with the C-arm of the C-arm system in any arbitrary location, a projection matrix for matching the 2D fluoroscopic image in relation to the 3D image is obtained, and the 2D fluoroscopic image is fused (matched) with the preoperative 3D image on the basis of the matching matrix and the projection matrix.

5 Claims, 3 Drawing Sheets

METHOD FOR MARKER-FREE AUTOMATIC FUSION OF 2-D FLUOROSCOPIC C-ARM IMAGES WITH PREOPERATIVE 3D IMAGES USING AN INTRAOPERATIVELY OBTAINED 3D DATA RECORD

BACKGROUND OF THE INVENTION

1. Field of the Invention

The present invention relates to a method for the superimposition of a preoperative 3D image over a 2D image obtained intraoperatively with a C-arm. In particular, the invention relates to the display of a 3D image representing a medical instrument that has been introduced into the area of examination of a patient and is contained within the 2D image.

2. Description of the Prior Art

Increasingly, patients are being examined and treated in a minimally invasive manner, i.e., with as little operative intrusion as possible. Examples of this approach are procedures using endoscopes, laparoscopes, or catheters, which are introduced into the examination or treatment region in the patient through a small body orifice. For example, catheters often are used in cardiology examinations.

From both a medical and a technical viewpoint, a problem is that although during the intervention (operation, examination) the medical instrument (the further text describes a catheter as a non-restrictive example) can be displayed very exactly and with a high resolution in one or more fluoroscopic images (also called 2D fluoroscopic images) using an intraoperative X-ray procedure with a C-arm, the 2D fluoroscopic images insufficiently display the anatomy of the patient. Furthermore, in the process of operation planning, the physician often wishes to display the medical instrument as a 3D image (3D data record) before the actual intervention (preoperative stage).

SUMMARY OF THE INVENTION

An object of the present invention is to fuse, in a simple manner, 2D fluoroscopic images, which have been obtained in an intraoperative procedure, and which display the medical instrument, with 3D images obtained in the preoperative stage.

According to the invention, this object is achieved by a method for a marker-free automatic fusion of 2D fluoroscopic C-arm images with preoperative 3D images using an intraoperatively obtained 3D data record characterized by the following steps.

An intraoperative 3D image is obtained using a C-arm x-ray apparatus. Image-based matching of an existing preoperative 3D image with relation to the intraoperative 3D image D is undertaken, which creates a matching matrix. A tool plate attached to the C-arm x-ray apparatus is matched in relation to a navigation system S. A 2D fluoroscopic image (designed to be matched) is obtained with the C-arm of the C-arm x-ray system in any C-arm position. A projection matrix LDC is determined that matches the 2D fluoroscopic image in relation to the intraoperative 3D image. The 2D fluoroscopic image is fused with the preoperative 3D image on the basis of the matching matrix and the projection matrix.

According to the invention, the preoperative 3D image is obtained in a first step.

The projection matrix preferably is obtained on the basis of a C-arm calibration.

According to the invention, when creating the projection matrix, look-up tables will take into consideration deformation of the C-arm.

The above object also is achieved in accordance with the invention by a C-arm device that is suitable for implementation of the method.

DESCRIPTION OF THE PREFERRED EMBODIMENTS

Figure 1:
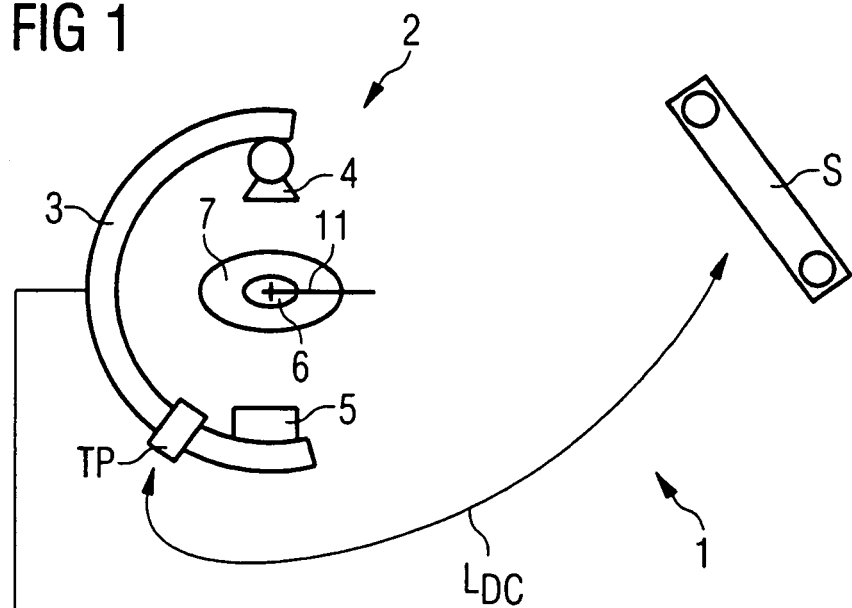
FIG. 1 is a schematic drawing of a medical examination and/or treatment device according to this invention.
Figure 1:
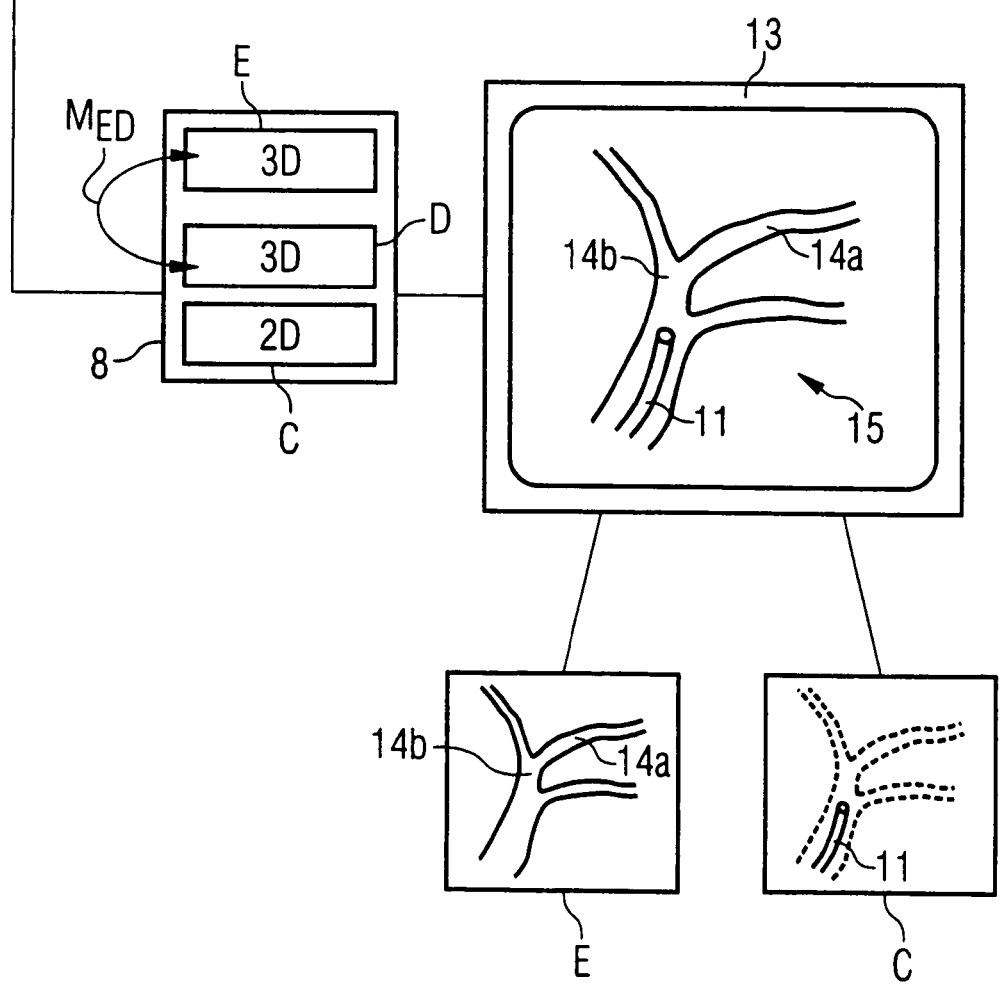

FIG. 1 is a schematic illustration of a medical examination and/or treatment device 1 according to this invention, wherein only the basic components are shown. The device has a data acquisition device 2 for obtaining two-dimensional X-ray images (2D fluoroscopic images). The data acquisition device has a C-arm 3 on which an X-ray source 4 and a radiation detector 5, for example, a solid-state image detector, are mounted, as well as a tool plate TP. The field of examination 6 of a patient 7 is preferably located in the isocenter of the C-arm 3, so that it is completely visible in the recorded 2D fluoroscopic image.

In close proximity to the data acquisition device 2 is a navigation sensor S, which detects the actual location of the tool plate TP—and thus the location of the C-arm 3—and the location and position of the medical instrument 11 used for the intervention, as well as the patient. If the locations of the device 2 and the patient are not required, the position of the C-arm 3 can be determined by means of the angle encoder of the C-arm 3. A navigation system then is not required.

The device 2 is operated by a control and processing device 8, which, among other things, also controls the image recording process. The control and processing device 8 has an image-processing unit that is not shown in detail. This unit contains, among other things, a 3D image data record E, which preferably has been recorded in the preoperative stage. This preoperative data record E can be recorded with any imaging modality, for example, with a computed tomography device CT, a magnetic resonance tomography device MRT, a positron emission tomography device PET, etc.

In the example shown, a catheter 11 is introduced into the field of examination 6, in this case, a heart. The location and position of this catheter 11 can be detected by the navigation system S—if used—and displayed in an intraoperative C-arm image (2D fluoroscopic image) C. Such an image is shown in FIG. 1 in the form of an enlarged schematic drawing.

The present invention provides a method by which an intraoperative 2D fluoroscopic image 10 obtained at any position of the C-arm 3 and containing in the medical instrument 11 (here a catheter) is automatically, i.e., by means of a computer in the processing unit 8, superimposed (fused) with the preoperative 3D image E so that a display and navigation of the instrument in the preoperative 3D data record E is possible. The result of such a fusion is represented in FIG. 1 in the form of the fused image 15 shown on the monitor 13.

In order to achieve a correct (i.e., in a proper relative position) fusion of intraoperative 2D fluoroscopic images with the preoperative 3D data record E, it is necessary to match the two images in relation to each other and/or in relation to the navigation sensor S. To match two image data records (of three-dimensional and/or two-dimensional nature) one must either correlate their respective coordinate systems with each other, or determine an imaging algorithm for converting one image data record into the other. In general, such an imaging algorithm, i.e., matching, is defined by a matrix. Other terms used for matching are, among others, "fusing" or "correlating." A user can do such matching, for example, interactively on a screen.

There are various possibilities of matching two images:

1. One may be able to identify one or preferably more image elements in the 2D fluoroscopic image and then identify the same image element(s) in the 3D image and consequently align this 3D image in relation with the 2D fluoroscopic image using translation and/or rotation and/or 2D projection. Such image elements are called "markers," and can be based on the patient's anatomy or selected artificially. Markers of an anatomical origin, such as the vessel bifurcation points, small sections of coronary arteries, or mouth corners and nose tips, are called "anatomical markers" or "anatomical landmarks." Artificially introduced marking points are called "artificial markers." Artificial markers are, for example, bolts that are installed in a preoperative intervention, or any other objects that are attached (for example, glued) to the surface of the examined body. The user can interactively define anatomical or artificial markers in the 2D fluoroscopic image (for example, by clicking on the screen), and subsequently search for them and identify them in the 3D image using a suitable analysis algorithm. Such matching is called "marker-based matching."

2. Another possibility is so-called "image-based matching." In this process, a 2D projection image is derived from a 3D image in the form of a digitally reconstructed radiogram (DRR). This image is then compared with the 2D fluoroscopic image from the viewpoint of their correlation, and subsequently the correlation is optimized by changing the DRR image by translation and/or rotation and/or by stretching until the agreement of the two images reaches a certain pre-defined minimum level. For this purpose, after its generation the DRR image is first put by the user into a position in which it is most similar to the 2D fluoroscopic image, and only then is the optimization cycle started, which reduces the computer time required for the matching process.

Figure 2:
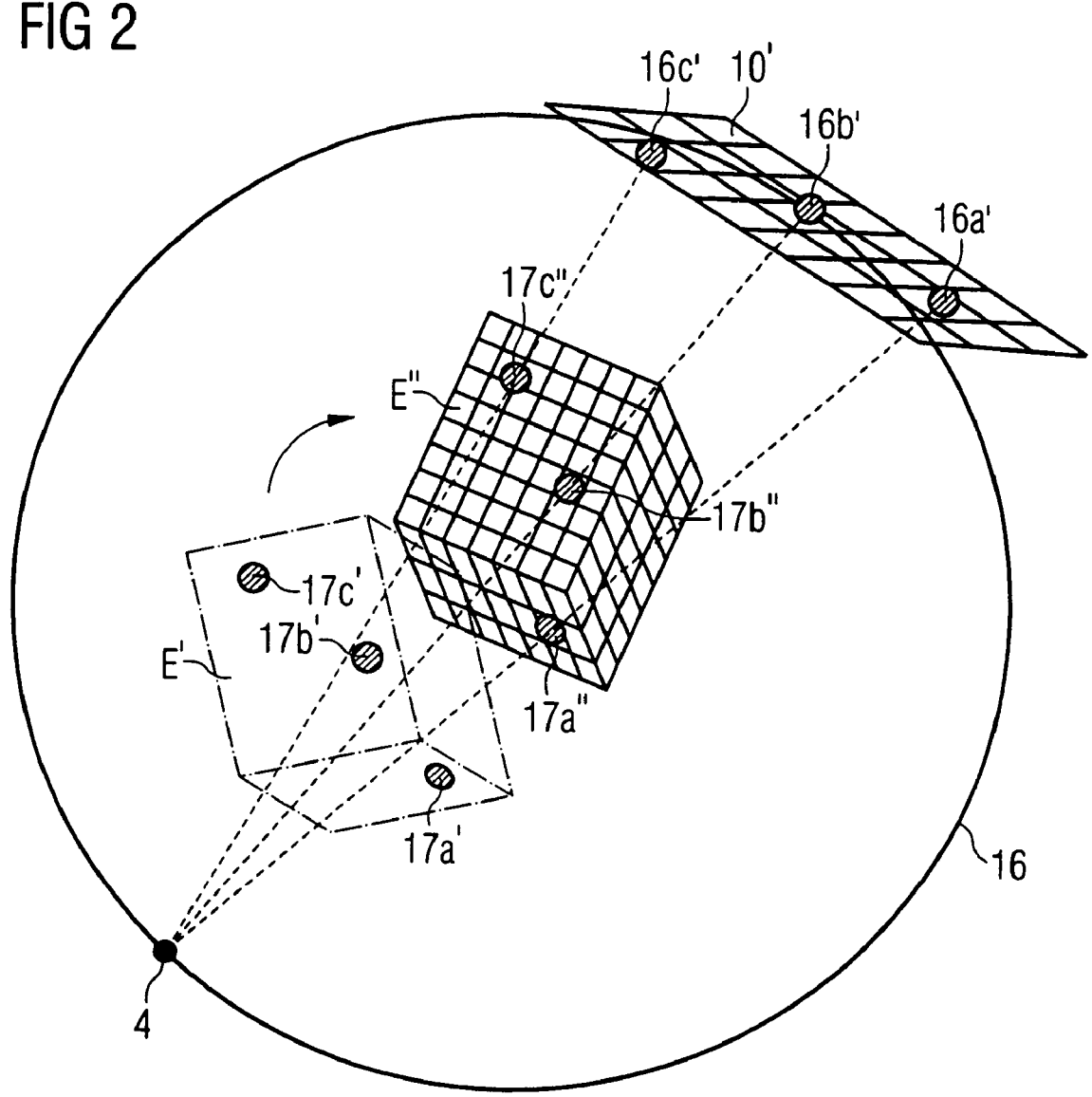
FIG. 2 is a schematic drawing to illustrate the marker-free matching of a 3D image with a 2D fluoroscopic image in accordance with the invention.

FIG. 2 shows a schematic drawing that illustrates the marker-based matching of a 3D image with a 2D fluoroscopic image. A 2D fluoroscopic image 10' is shown, which was detected by detector 5 installed in the same location but not shown here. Further shown is the radiation source 4 and/or its focus and the movement trajectory 16 of the C-arm 3 around which the detector 5 and the radiation source 4 are moved.

Also shown is the original 3D image E' as it appears immediately after its generation without having been matched in relation to the 2D fluoroscopic image 10'.

To allow for matching, several markers (in the shown example, it is three spherical artificial markers 16a', 16b', and 16c') are identified, i.e., defined in the 2D fluoroscopic image 10'. These markers are then also identified in the original 3D image E'. As can bee seen from FIG. 2, the markers 17a', 17b', and 17c' of the original 3D image are located in such places where they do not lie directly in the projection lines that run from the radiation source 4 to the markers 16a', 16b', 16c' in the 2D fluoroscopic image 10'. Had the markers 17a', 17b', and 17c' been projected on the detector plane, they would lie in substantially different places than the markers 16a', 16b', and 16c'.

To achieve proper matching, the 3D image E' is moved by translation and rotation (in this example, no stretching is required) until the markers 17a", 17b", and 17c" of the de-positioned 3D image E" can be projected onto the markers 16a', 16b', 16c', and thus the matching is completed.

Both the image-based and the marker-based matching techniques have substantial disadvantages: A marker-based matching frequently requires an additional operative intervention to introduce artificial markers. Anatomical markers are often difficult to uniquely define (locate), which is why the calibration of marker-based matching is often prone to errors. The image-based matching technique requires very long computing times and, due to numerical instability, it is a very unsafe method if the two images to be matched are very much different from each other.

The identification of the markers during the marker-based matching need not necessarily be done on a screen. If a navigation system is present (navigation sensor S, see FIG. 1), to prepare a navigation-supported surgical intervention, the physician performs the marker-based matching of, for example, a preoperative 3D image in relation to the navigation system S by manually touching artificial or anatomical markers with a navigation pointer. Since, due to the existing detectors, the medical instrument 11 is matched in relation to the navigation system as for its location and position, this establishes a correlation between the medical instrument 11 and the preoperative 3D image E. Thus, using the control and processing device 8, the actual relevant image of the medical instrument 11 can be integrated and visually collimated into the 3D image. This allows for the navigation of the medical instrument in E.

Nevertheless, a navigation-supported matching technique also has substantial disadvantages: If it is desired to match, using the navigation-based method, intraoperatively measured 2D fluoroscopic images with the preoperative 3D image, during the navigation-supported marker-based matching, the markers would again have to be manually touched for each C-arm position of the 2D fluoroscopic image to be recorded. In practice, such a procedure is very much prone to errors and is rather awkward. If the markers in the image are touched in a different order than in those attached to the patient, or if the anatomical markers are started in a non-reproducible manner, or if the relative position of the markers has changed, a wrong positioning will result. In addition, in the case of a misalignment of the navigation during the intervention, the matching must be repeated.

Conventional marker-based or image-based matching thus has many disadvantages.

The method according to this invention utilizes the fact that a preoperative 3D image differs only very little from an intraoperative 3D image that has been recorded in the 3D angiography mode of a C-arm device. Thus, the basis of the invention is that—before recording a 2D fluoroscopic image C to be matched with the preoperative 3D image E—using the C-arm 3, an intraoperative 3D image D is acquired, which can be matched in an image-based manner with the preoperative 3D image E using known (for example, the above-described) methods. The matching matrix underlying this matching process can be determined by an image-based 3D—3D matching technique using known methods (partially described above).

Using an algorithm for the projection of a 2D fluoroscopic image C, obtained intraoperatively in any position of the C-arm, onto the intraoperative 3D image D, the 2D fluoroscopic image C can be matched with the preoperative 3D data record E without the use of any markers. Thus, the problems associated with marker-based matching are circumvented.

None of the subsequent 2D–3D fusions required during the intervention or examination require any interactive matching, as will be explained in the following text using the process flowchart in FIG. 3.

Figure 3:
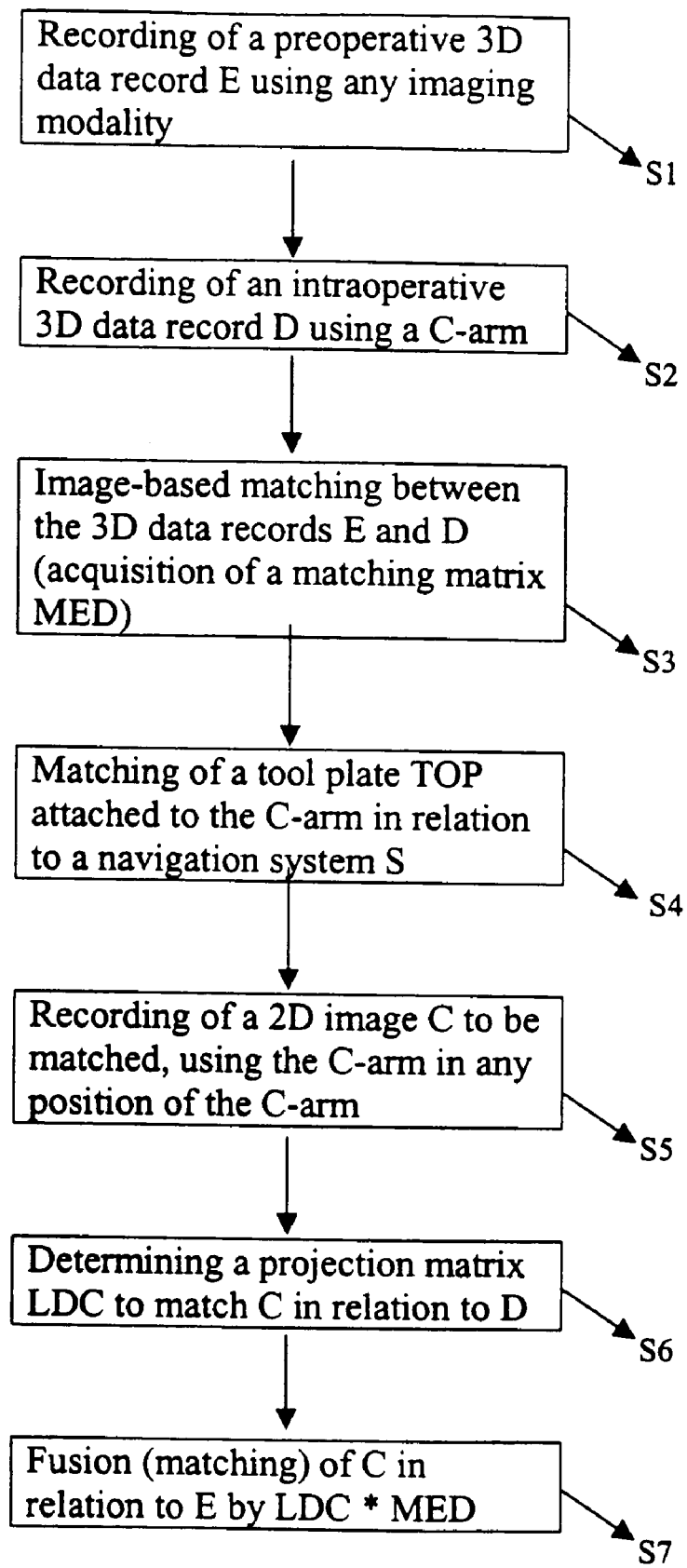
FIG. 3 is a flowchart of an embodiment of the method according to the invention.

FIG. 3 schematically shows the procedure of the present invention for an automatic marker-free fusion of intraoperative 2D fluoroscopic images with preoperative 3D images involving the one-time use of image-based 3D—3D matching. This embodiment of the method includes seven steps:

In the first step S1, a preoperative 3D data record E is recorded. The 3D data record can be recorded with any imaging modality (MRT, CT, PET, US, etc.). In the second step S2, an intraoperative 3D image D is recorded using a C-arm. For the purpose of such a recording, the C-arm is preferably operated in 3D angiography mode, which later allows one to determine, in a simple manner, the correlation (projection) between this intraoperative 3D image D and any 2D image C recorded with the same C-arm. In the, third step S3, an image-based matching between the two 3D data records E and D is performed. This image-based matching is done on the basis of a matching matrix $M_{ED}$, which is determined by means of image-based matching. In the fourth step S4, a tool plate TP attached to the C-arm is matched in relation to a navigation system S. If there is no navigation system available, the location of the C-arm during the matching of the tool plate TP is determined by an angle-encoder mounted on the C-arm. In the fifth step S5, a 2D fluoroscopic image to be matched is measured with the C-arm in any position of the C-arm. In the sixth step S6, a projection algorithm in the form of a projection matrix LDC is found for the matching of C in relation to D. In the seventh and last step S7, using $L_{DC}*M_{ED}$, the intraoperative 2D fluoroscopic image C is fused (matched) with the preoperative 3D image E.

The projection matrix $L_{DC}*$ is essentially defined by the C-arm calibration (performed once before the C-arm device is shipped). So, for example, with a 2D fluoroscopic image recording in a C-arm angulation of 0°, and the corresponding orbital angle 0°, the location of the c-arm is accurately defined (a calibration at 0° angulation is usually performed in 1° orbital angle steps). The method according to the invention uses that projection matrix which is closest to the calibrated projection matrix. During the process of determining the projection matrix at an angulation ≠0°, a non-linear distortion or deformation of the C-arm occurs as a result of its own weight, which must be taken into consideration. For each concrete angulation angle with its corresponding orbital angle, the C-arm deformation can be taken into consideration and thus corrected.

The inventive method and apparatus avoid the problems associated with marker-based matching.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for automatic marker-free matching of 2D fluoroscopic C-arm images with preoperative images using an intraoperatively acquired 3D record, comprising the steps of:
   during a medical interventional procedure involving a region of a patient, intraoperatively obtaining a 3D image of the region using a C-arm x-ray system having a C-arm and having a tool plate attached to the C-arm x-ray system;
   undertaking an image-based matching of an existing preoperative 3D image of the region, obtained prior to said medical interventional procedure, relative to the intraoperative 3D image, and thereby generating a matching matrix;
   matching the tool plate relative to a navigation system;
   obtaining a 2D fluoroscopic image using said C-arm x-ray system with said C-arm at any arbitrary position;
   determining a projection matrix for matching said 2D fluoroscopic image to said 3D image; and
   matching said 2D fluoroscopic image with said preoperative 3D image using said matching matrix and said projection matrix.

2. A method as claimed in claim 1 comprising, prior to said medical interventional procedure, obtaining said preoperative 3D image of said region.

3. A method as claimed in claim 1 comprising acquiring said projection matrix during a calibration of said C-arm x-ray system.

4. A method as claimed in claim 1 wherein said C-arm of said C-arm x-ray system exhibits deformation, and taking said deformation into account, using a look-up table, for determining said projection matrix.

5. A C-arm x-ray apparatus comprising:
   a C-arm on which an x-ray source and a radiation detector are mounted adapted for irradiating a region of a patient during a medical interventional procedure;
   a tool plate mounted to said C-arm;
   a navigation system; and
   a control and operating unit for operating said C-arm, said x-ray source and said radiation detector, and for receiving signals from said navigation system, for during a medical interventional procedure involving a region of a patient, intraoperatively obtaining a 3D image of the region using a C-arm x-ray system having a C-arm and having a tool plate attached to the C-arm x-ray system, undertaking an image-based matching of an existing preoperative 3D image of the region, obtained prior to said medical interventional procedure, relative to the intraoperative 3D image, and thereby generating a matching matrix, matching the tool plate relative to a navigation system, obtaining a 2D fluoroscopic image using said C-arm x-ray system with said C-arm at any arbitrary position, determining a projection matrix for matching said 2D fluoroscopic image to said 3D image, and matching said 2D fluoroscopic image with said preoperative 3D image using said matching matrix and said projection matrix.

* * * * *